United States Patent [19]
McLain et al.

[11] Patent Number: 5,852,145
[45] Date of Patent: Dec. 22, 1998

[54] POLYMERIZATION PROCESSES FOR OLEFINS

[75] Inventors: Stephan James McLain, Wilmington; Jerald Feldman, Hockessin, both of Del.

[73] Assignee: E. I. du Pont de Nemours and Company, Wilmington, Del.

[21] Appl. No.: 897,805

[22] Filed: Jul. 21, 1997

Related U.S. Application Data

[60] Provisional application No. 60/022,295, Jul. 23, 1996 and provisional application No. 60/022,796, Jul. 30, 1996.

[51] Int. Cl.[6] .................................................. C08F 4/70

[52] U.S. Cl. ...................... 526/133; 526/151; 526/161; 526/160; 526/122; 526/139; 526/141; 526/308; 526/348.5; 526/352; 526/281; 526/348.2; 525/269; 525/270

[58] Field of Search ...................... 526/133, 151, 526/160, 161, 122, 139, 141; 525/269, 270

[56] References Cited

FOREIGN PATENT DOCUMENTS

WO96/23010  1/1996  WIPO ........................ C08F 210/16

OTHER PUBLICATIONS

PCT International Search Report for PCT/US 97/12801 (CR9969) dated Dec. 9, 1997.

Michael Svoboda and Heindirk tom Dieck, Diazadien–Nickel–Alkyle, *Journal of Organometallic Chemistry*, 191, 321–328, 1980.

Lynda K. Johnson, Christopher M. Killian, and Maurice Brookhart, New Pd(II)– and Ni(II)–Based Catalysts for Polymerization of Ethylene and α–Olefins, *J. Am. Chem. Soc.,* 117, 6414–6415, 1995.

Rob van Asselt, Cornelis J. Elsevier, Wilbert J. J. Smeets, Anthony L. Spek and Roland Benedix, Synthesis and characterization of rigid bidentate nitrogen ligands and some examples of coordination to divalent palladium. X–ray crystal structures of bis(p–tolylimino)acenaphthene and methylchloro[bis(o, o'–diisopropylphenyl–imino)acenaphthene]palladium(II), *Recl. Trav. Chim. Pays–Bas,* 113, 88–98, 1994.

*Primary Examiner*—Mark Nagumo
*Attorney, Agent, or Firm*—Craig H. Evans; Joel D. Citron

[57] ABSTRACT

Certain olefins such as ethylene, α-olefins and cyclopentene can be polymerized by using catalyst system containing a nickel or palladium α-diimine complex, a metal containing hydrocarbylation compound, and a selected Lewis acid, or a catalyst system containing certain nickel [II] or palladium [II] compounds, an α-diimine, a metal containing hydrocarbylation compound, and optionally a selected Lewis acid. The process advantageously produces polyolefins useful for molding resins, films, elastomers and other uses.

19 Claims, No Drawings

POLYMERIZATION PROCESSES FOR OLEFINS

This application claims the benefit of U.S. Provisional Application No. 60/022,295 filed Jul. 23, 1996, and U.S. Provisional Application No. 60/022,796, filed Jul. 30, 1996.

FIELD OF THE INVENTION

Disclosed herein are processes for polymerizing selected olefins, by contacting them with certain nickel or palladium compounds, other selected compounds, and if the nickel or palladium compound is not already an α-diimine complex, a free α-diimine.

TECHNICAL BACKGROUND

Polyolefins are important items of commerce, many thousands of tons being produced annually. They are useful in many applications depending upon their particular properties, for instance as molding resins, fibers, films useful in packaging and/or electronics, elastomers, and many others. There are many known polymerization processes for producing polyolefins, but given the importance of these polymers, improved processes are constantly being sought.

L. K. Johnson, et. al., J. Am. Chem. Soc., vol. 117, p. 6414–6415 (1995), and L. K. Johnson, et al., J. Am. Chem. Soc., vol. 118, p. 267–268 (1996) describe the polymerization of olefins using certain α-diimine complexes. Neither of these references describes a polymerization process using the starting materials described herein.

SUMMARY OF THE INVENTION

Described herein is a first process for the polymerization of olefins, comprising, contacting, at a temperature of about −100° C. to about +200° C., a Ni (II) or Pd (II) complex of (I),

a metal containing hydrocarbylation compound, and a compound (II) selected from the group consisting of $B(C_6F_5)_3$, $AlCl_3$, $AlBr_3$, $Al(OTf)_3$, and $(R^{13}R^{14}R^{15}C)Y$, with an olefin, wherein:

said olefin is selected from the group consisting of ethylene, an olefin of the formula $R^{17}CH=CH_2$ or $R^{17}CH=CHR^{17}$, cyclobutene, cyclopentene, and a norbornene;

$R^2$ and $R^5$ are each independently aryl or substituted aryl, provided in both $R^2$ and $R^5$ at least one of the carbon atoms bound to a carbon atom bound directly to an imino nitrogen atom does not have any hydrogen atoms bound to it;

$R^3$ and $R^4$ are each independently hydrogen, hydrocarbyl, substituted hydrocarbyl, or $R^3$ and $R^4$ taken together are hydrocarbylene or substituted hydrocarbylene to form a carbocyclic ring;

$R^{13}$, $R^{14}$ and $R^{15}$ are each independently aryl or substituted aryl;

each $R^{17}$ is independently hydrocarbyl or substituted hydrocarbyl provided that any olefinic bond in said olefin is separated from any other olefinic bond or aromatic ring by a quaternary carbon atom or at least two saturated carbon atoms; and Y is a relatively noncoordinating anion.

This invention also concerns a second process for the polymerization of olefins, comprising, contacting a Ni (II) or Pd (II) salt with (I),

a metal containing hydrocarbylation compound, and optionally a compound (II) selected from the group consisting of $B(C_6F_5)_3$, $AlCl_3$, $AlBr_3$, $Al(OTf)_3$, and $(R^{13}R^{14}R^{15}C)Y$, with an olefin, wherein:

said Ni (II) or Pd (II) salt is selected from the group consisting of $Ni(O_2CR^7)_2$, $Ni[R^8COCH=C(O)R^8]_2$, $NiX_2$, $L^1L^2NiX_2$, $Ni(OR^{18})_2$, $Pd(O_2CR^9)_2$, $Pd[R^{10}COCH=C(O)R^{10}]_2$, $PdX_2$, $L^1L^2PdX_2$, and $Pd(OR^{19})_2$;

said olefin is selected from the group consisting of ethylene, an olefin of the formula $R^{17}CH=CH_2$ or $R^{17}CH=CHR^{17}$, cyclobutene, cyclopentene, and a norbornene;

$R^2$ and $R^5$ are each independently aryl or substituted aryl, provided in both $R^2$ and $R^5$ at least one of the carbon atoms bound to a carbon atom bound directly to an imino nitrogen atom does not have any hydrogen atoms bound to it;

$R^3$ and $R^4$ are each independently hydrogen, hydrocarbyl, substituted hydrocarbyl, or $R^3$ and $R^4$ taken together are hydrocarbylene or substituted hydrocarbylene to form a carbocyclic ring;

$R^{13}$, $R^{14}$ and $R^{15}$ are each independently aryl or substituted aryl;

each $R^{17}$ is independently hydrocarbyl or substituted hydrocarbyl provided that any olefinic bond in said olefin is separated from any other olefinic bond or aromatic ring by a quaternary carbon atom or at least two saturated carbon atoms; and each $R^{18}$ and $R^{19}$ is independently hydrocarbyl, substituted hydrocarbyl, or $R^{21}SO_3^-$;

each $R^7$, $R^8$, $R^9$ and $R^{10}$ is independently hydrocarbyl or substituted hydrocarbyl containing from 1 to 20 carbon atoms;

each X is independently halogen or $R^{21}SO_3^-$;

each $R^{21}$ is independently aryl, substituted aryl or perfluoroalkyl;

$L^1$ and $L^2$ are ligands capable of being displaced by (I), or taken together are a bidentate ligand that is capable of being displaced by (I); and Y is a relatively noncoordinating anion;

and provided that when said hydrocarbylation compound is other than an alkylaluminum compound containing one or more halogen atoms bound to an aluminum atom or $(R^{20}AlO)_q$ wherein $R^{20}$ is alkyl and q is a positive integer, (II) must be present.

Described herein is a novel compound of the formula

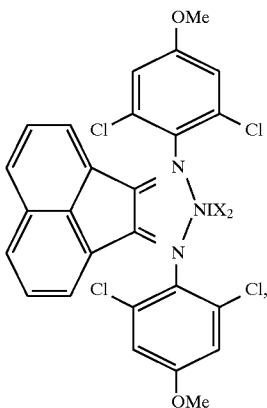

wherein each X is independently halogen, $R^7CO_2$, $R^8COCH=C(O)R^8$, or $OR^{18}$, each $R^{18}$ is independently hydrocarbyl, and $R^7$, $R^8$ are hydrocarbyl or substituted hydrocarbyl containing from 1 to 20 carbon atoms.

Also disclosed is a compound of the formula

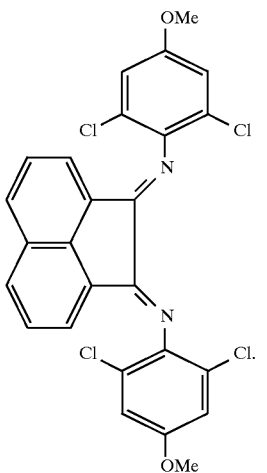

DETAILS OF THE INVENTION

Herein certain terms are used to define certain chemical groups or compounds. These terms are defined below.

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By an alkyl aluminum compound is meant a compound in which at least one alkyl group is bound to an aluminum atom. Other groups such as alkoxide, oxygen, and halogen may also be bound to aluminum atoms in the compound.

By "hydrocarbylene" herein is meant a divalent group containing only carbon and hydrogen. Typical hydrocarbylene groups are $-(CH_2)_4-$, $-CH_2CH(CH_2CH_3)CH_2CH_2-$ and

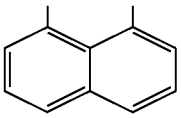
(An)

If not otherwise stated, it is preferred that hydrocarbylene groups herein contain 1 to about 30 carbon atoms.

By "substituted hydrocarbylene" herein is meant a hydrocarbylene group which contains one or more substituent groups which are inert under the process conditions to which the compound containing these groups is subjected. The substituent groups also do not substantially interfere with the process. If not otherwise stated, it is preferred that substituted hydrocarbylene groups herein contain 1 to about 30 carbon atoms. Included within the meaning of "substituted" are heteroaromatic rings.

By "a norbornene" is meant that the monomer is characterized by containing at least one norbornene-functional group in its structure including norbornadiene as identified by the formulas below, which can be substituted or unsubstituted

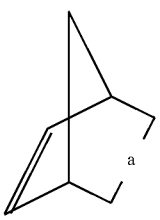
(XXXIV)

wherein "a" represents a single or double bond.

Representative monomers are compounds (XXXV) and (XXXX) as follows:

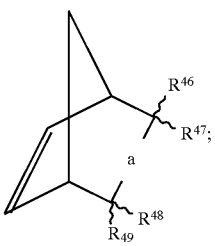
(XXXV)

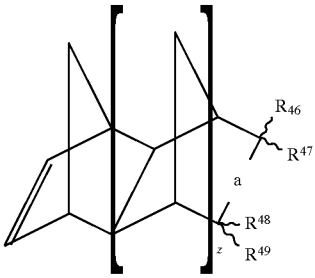
(XXXX)

wherein $R^{46}$, $R^{47}$, $R^{48}$, and $R^{49}$ independently are hydrogen halogen, or hydrocarbyl, provided that, except if the hydrocarbyl group is vinyl, if any of the hydrocarbyl are alkenyl, there is no terminal double bond, i.e., the double bond is internal; or $R^{46}$ and $R^{48}$ taken together can be part of carbocyclic ring (saturated, unsaturated or aromatic); or $R^{46}$ and $R^{47}$ and/or $R^{48}$ and $R^{49}$ taken together are an alkylidene group. In these structures "z" is 1 to 5.

Examples of such norbornenes include norbornadiene, 2-norbornene, 5-methyl-2-norbornene, 5-hexyl-2-norbornene, 5-ethylidene-2-norbornene, vinylnorbornene, dicyclopentadiene, dihydrodicyclopentadiene, tetracyclododecene, trimers of cyclopentadiene, halogenated norbornenes wherein $R^{46}$, $R^{47}$, $R^{48}$ and $R^{49}$ may also be halogen or fully halogenated alkyl groups such as $C_wF_{2w+1}$ wherein w is 1 to 20, such as perfluoromethyl and perfluorodecyl.

The halogenated norbornenes can be synthesized via the Diels-Alder reaction of cyclopentadiene an appropriate dieneophile, such as $F_3CC \equiv CCF_3$ or $R^{49}{}_2C=CR^{49}C_wF_{2w+1}$ wherein each $R^{49}$ is independently hydrogen or fluorine and w is 1 to 20.

By "saturated hydrocarbyl" is meant a univalent group containing only carbon and hydrogen which contains no unsaturation, such as olefinic, acetylenic, or aromatic groups. Examples of such groups include alkyl and cycloalkyl. If not otherwise stated, it is preferred that saturated hydrocarbyl groups herein contain 1 to about 30 carbon atoms.

By "aryl" is meant a monovalent radical which is one or more carbocyclic aromatic rings, and wherein the free bond is to a carbon atom of an aromatic ring. By "substituted aryl" is meant an aryl group substituted with one or more substituents which do not interfere with the polymerization reaction. Phenyl is a preferred aryl group for $R^{13}$, $R^{14}$ and $R^{15}$.

Herein the group "OTf" means a perfluoroalkylsulfonate anion containing 1 to 20 carbon atoms. A preferred perfluoroalkylsulfonate anion is trifluoromethanesulfonate (sometimes "triflate").

By "α-olefin" is meant a compound of the formula $CH_2=CHR^{19}$, wherein $R^{19}$ is n-alkyl or branched n-alkyl, preferably n-alkyl.

By "linear α-olefin" is meant a compound of the formula $CH_2=CHR^{19}$, wherein $R^{19}$ is n-alkyl. It is preferred that the linear α-olefin have 4 to 40 carbon atoms.

By a "saturated carbon atom" is meant a carbon atom which is bonded to other atoms by single bonds only. Not included in saturated carbon atoms are carbon atoms which are part of aromatic rings.

By a quaternary carbon atom is meant a saturated carbon atom which is not bound to any hydrogen atoms. A preferred quaternary carbon atom is bound to four other carbon atoms.

By an olefinic bond is meant a carbon-carbon double bond, but does not include bonds in aromatic rings.

By a "polymerization process" herein (and the polymers made therein) is meant a process which produces a polymer with a degree of polymerization (DP) of about 20 or more, preferably about 40 or more. By "DP" is meant the average number of repeat (monomer) units in the polymer.

By a metal containing hydrocarbylation compound is meant a compound which can transfer a hydrocarbyl group to a nickel or palladium compound. One form of this compound is commonly called an alkylating agent or compound in organic chemistry. Generally the hydrocarbyl group is thought of being present in the compound as an anion. Useful alkylating agents have the formula $MX_mR^6{}_n$ or $[Al(O)R^{11}]_q$, wherein M is a metal, preferably Li, Mg, Zn[II], Al, or Sn[IV]; each X is independently F, Cl, Br, I, or $OR^{12}$; each $R^6$ is independently hydrocarbyl containing from 1 to 20 carbon atoms; m is zero or greater and n is 1 or greater, and m+n is the valence of M and if the valence of M is 1, then m is 0; $R^{11}$ and $R^{12}$ are each independently hydrocarbyl, preferably alkyl, containing 1 to 20 carbon atoms; and q is a positive integer. It is preferred that $R^{11}$ is methyl.

By a weakly coordinating anion herein is meant an anion that does not coordinate strongly to a nickel or palladium cationic complex. The coordinating ability of such anions is known and has been discussed in the literature, see for instance W. Beck., et al., Chem. Rev., vol. 88 p. 1405–1421 (1988), and S. H. Strauss, Chem. Rev., vol. 93, p. 927–942 (1993), both of which are hereby included by reference. In addition to these "traditional" weakly coordinating anions, heterogeneous anions may also be employed. In these cases, the true nature of the counterion is poorly defined or unknown. A wide variety of heterogeneous inorganic materials can be made to function as non-coordinating counterions. Examples include aluminas, silicas, silica/aluminas, cordierites, clays, MgCl2, and many others utilized as traditional supports for Ziegler-Natta olefin polymerization catalysts. These are generally materials which have Lewis or Bronsted acidity. High surface area is usually desired and often these materials will have been activated through some heating process. Heating may remove excess surface water and change the surface acidity from Bronsted to Lewis type. Materials which are not active in the role may often be made active by surface treatment. For instance, a surface-hydrated silica, zinc oxide or carbon can be treated with an alkylaluminum compound to provide the required functionality.

Preferred relatively noncoordinating anions are BAF, $BF_4$, $SbF_6$, $B(C_6F_5)_4$ and $PF_6$. Herein BAF is an abbreviation for the tetrakis[3,5-bis(trifluoromethyl)phenyl]borate.

It is preferred that each $R^{18}$ and $R^{19}$ is independently hydrocarbyl, each $R^7$, $R^8$, $R^9$ and $R^{10}$ is independently hydrocarbyl, and/or each X is independently halogen, more preferably chlorine or bromine. When present it is preferred that $R^{21}$ is trifluoromethanesulfonate, phenyl or tolyl.

In both of the polymerization processes described herein compound (I) or a complex of it is present initially. In (I) $R^2$ and R5 are each independently aryl or substituted aryl, provided in both $R^2$ and $R^5$ at least one of the carbon atoms bound to a carbon atom bound directly to an imino nitrogen atom does not have any hydrogen atoms bound to it. In practice this means that in $R^2$ and $R^5$ the carbon atom ortho or adjacent to the carbon atom which is bound to an imino nitrogen atom must be substituted. Suitable groups for $R^2$ and $R^5$ include 2-methylphenyl, 2-phenylphenyl, 2,6-diisoproylphenyl, 1-naphthyl, 1-methyl-2-naphthyl, 1-anthracenyl, and 9-anthracenyl. Aryl groups that are not suitable include phenyl, 2-naphthyl, and 3-ethylphenyl.

Preferred combinations of groups for $R^2$, $R^3$, $R^4$ and $R^5$ are given in the following Table.

| $R^2$ | $R^3$ | $R^4$ | $R^5$ |
| --- | --- | --- | --- |
| 2,6-i-PrPh | H | H | 2,6-i-PrPh |
| 2,6-i-PrPh | Me | Me | 2,6-i-PrPh |
| 2,6-i-PrPh | An | An | 2,6-i-PrPh |
| 2,6-MePh | H | H | 2,6-MePh |
| 2,6-EtPh | Me | Me | 2,6-EtPh |
| 2,4,6-MePh | Me | Me | 2,4,6-MePh |
| 2,6-MePh | Me | Me | 2,6-MePh |

-continued

| R² | R³ | R⁴ | R⁵ |
|---|---|---|---|
| 2,6-MePh | An | An | 2,6-MePh |
| 2-t-BuPh | An | An | 2-t-BuPh |
| 2,5-t-BuPh | An | An | 2,5-t-BuPh |
| 2,4,6-MePh | An | An | 2,4,6-MePh |
| 2-Cl-6-MePh | Me | Me | 2-Cl-6-MePh |
| 2,6-Cl-4-OMePh | Me | Me | 2,6-Cl-4-OMePh |
| 2,6-Cl-4-OMePh | An | An | 2,6-Cl-4-OMePh |
| 2-i-Pr-6-MePh | An | An | 2-i-Pr-6-MePh |
| 2-i-Pr-6-MePh | Me | Me | 2-i-Pr-6-MePh |
| 2,6-t-BuPh | H | H | 2,6-t-BuPh |
| 2,6-t-BuPh | Me | Me | 2,6-t-BuPh |
| 2,6-t-BuPh | An | An | 2,6-t-BuPh |
| 2-t-BuPh | Me | Me | 2-t-BuPh |

Herein Me is methyl, Et is ethyl, Pr is propyl, Bu is butyl, Ph is phenyl, OMe is methoxy, and An is 1,8-naphthylylene. Any of the groups shown in the above table may also be mixed in any fashion to achieve other combinations.

In certain situations "unsymmetrical" α-diimine ligands of formula (I) are also preferred. In particular when $R^2$ and $R^5$ are phenyl, and one or both of these is substituted in such a way as different sized groups are present in the 2 and 6 position of the phenyl ring(s) unusual polymers may be produced, for instance if one or both of $R^2$ and $R^5$ are 2-t-butylphenyl. In this context when $R^2$ and/or $R^5$ are "substituted" phenyl the substitution may be not only in the 2 and/or 6 positions, but on any other position in the phenyl ring. For instance, 2,5-di-t-butylphenyl, and 2-t-butyl-4,6-dichlorophenyl would be included in substituted phenyl.

The steric effect of various groupings has been quantified by a parameter called $E_s$, see R. W. Taft, Jr., J. Am. Chem. Soc., vol. 74, p. 3120–3128, and M. S. Newman, Steric Effects in Organic Chemistry, John Wiley & Sons, New York, 1956, p. 598–603. For the purposes herein, the $E_s$ values are those for o-substituted benzoates described in these publications. If the value for $E_s$ for any particular group is not known, it can be determined by methods described in these publications. For the purposes herein, the value of hydrogen is defined to be the same as for methyl. It is preferred that difference in $E_s$, when $R^2$ (and preferably also $R^5$) is phenyl, between the groups substituted in the 2 and 6 positions of the phenyl ring is at least 0.15, more preferably at least about 0.20, and especially preferably about 0.6 or more. These phenyl groups may be unsubstituted or substituted in any other manner in the 3, 4 or 5 positions. These differences in $E_s$ are preferred in (I), and in both of the polymerization processes herein.

It will be understood by the artisan that not every possible compound (I) or its Ni or Pd complex will be active in polymerizations of every olefin listed herein, but that the vast majority will be active in such polymerizations. Special steric or electronic features in (I) combined with the structure of the olefin may prevent polymerization in a few cases. However the determination of whether a particular α-diimine or its Ni or Pd complex will be active in polymerization with a certain olefin requires minimal experimentation to determine, see for instance the polymerization Examples herein.

Preferred olefins in both polymerizations are one or more of ethylene, propylene, 1-butene, 2-butene, 1-hexene 1-octene, 1-pentene, 1-tetradecene, norbornene, and cyclopentene, with ethylene, propylene and cyclopentene being more preferred. Ethylene and cyclopentene (alone as homopolymers) are especially preferred. Another preferred type of olefin is an α-olefin, and a linear α-olefin is especially preferred. When norbornene is used as a monomer it is preferred that it be the only olefin present.

Random copolymers may be made with these polymerization processes by the simultaneous polymerization of 2 or more olefins. Block copolymers may be made (particularly at subambient temperatures, preferably about −30° C. to 0° C.) by sequential polymerization of the monomer(s) of each block in the polymer.

It has been found that compound 4,

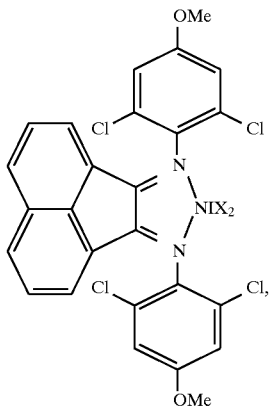

when used for polymerization of cyclopentene, gives a tractable cyclopentene with the highest melting point yet achieved. X is preferably chlorine or bromine. This compound may be used in the first polymerization process. It is made from compound (VII), or (VII) may be used directly in the second polymerization process.

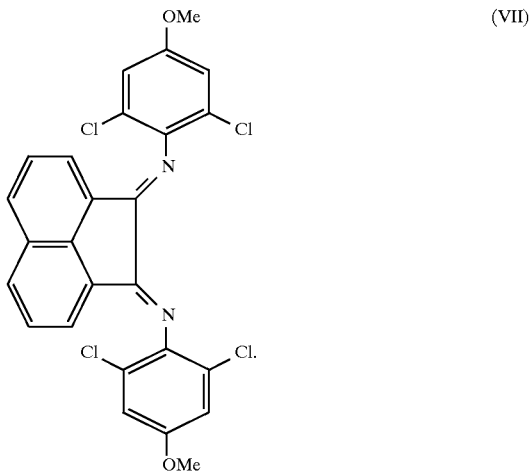

In both 4 and (VII) the methoxy group may be replaced by an alkoxy group wherein the alkoxy group contains 2 to 20 carbon atoms.

The temperature at which the polymerization processes are carried out is about −100° C. to about +200° C., preferably about 0° C. to about 150° C., more preferably about 25° C. to about 100° C. The pressure at which the polymerization is carried out (for a gaseous monomer) is not critical, atmospheric pressure to about 275 MPa being a suitable range. The pressure can affect the microstructure of the polyolefin produced.

A preferred compound (II) is $(C_6F_5)_3B$. When (II) is $(R^{13}R^{14}R^{15}C)Y$ it is preferred that all of $R^{13}$, $R^{14}$ and $R^{15}$ are phenyl. It will be understood by the artisan that (II) is preferably a Lewis acid-type compound.

In the second polymerization process, when a hydrocarbylation compound is other than an alkylaluminum compound containing one or more halogen atoms bound to an aluminum atom or an alkyl aluminoxane, (II) must be present. Thus when the hydrocarbylation compound is R₃Al (II) must be present. When the hydrocarbylation compound is R₂AlBr, RAlCl₂, or "RAlO", (II) may optionally be present (R in these last two sentences is alkyl).

In the first process, when a Ni[II] or Pd[II] complex of (I) is used, a preferred structure for the complex is

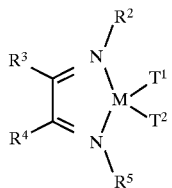
(VI)

wherein M is Ni or Pd, $R^2$, $R^3$, $R^4$ and $R^5$ are as defined as above and $T^1$ and $T^2$ are each independently halogen, $R^7CO_2$, $R^8COCH=C(O)R^8$, $OR^{18}$ wherein $R^7$, $R^8$ and $R^{18}$ are as defined above. It is preferred that $T^1$ and $T^2$ are chlorine and/or bromine.

In both polymerization processes, molar ratios of the various ingredients are not critical, but for good yields of polymer and/or to minimize cost of ingredients, certain ratios are preferred. In the first polymerization process it is preferred that the ratio of number of moles of olefin: "moles" of Pd or Ni present be greater that 3,000, preferably about 5,000 or more. The molar ratio of (II): Pd or Ni is preferably about 0.5 to about 10, more preferably about 1 to about 5. The molar ratio of hydrocarbylation compound: Pd or Ni is preferably about 0.5 to about 200, more preferably about 20 to about 100, in the second polymerization process when (II) is not present. In the first polymerization process, or in the second polymerization process when (II) is present, the molar ratio of hydrocarbylation compound: Pd or Ni is preferably about 0.5 to about 20, more preferably about 1 to about 10.

When the ingredients for the polymerization are first mixed to initiate the polymerization it is preferred that they be mixed in a liquid medium, preferably a liquid medium in which at least one of the ingredients other than the olefin is at least slightly soluble. For instance the polymerization of cyclopentene may be carried out in neat cyclopentene or in a mixture of 1,2,4-trichlorobenzene and cyclopentene. The polymerization itself may then be carried out in solution (the polymer soluble in the medium), slurry, or even the gas phase with droplets containing the active catalyst suspended in, for example, gaseous olefin.

The polymerization may be carried out in any of the usual ways, such as a batch, semi-batch or continuous operation. The latter for example may be a continuous stirred tank reactor, which is well known in the art.

These polymerization processes have advantages over those processes reported in L. K. Johnson, et. al., J. Am. Chem. Soc., vol. 117, p. 6414–6415 (1995), and L. K. Johnson, et al., J. Am. Chem. Soc., vol. 118, p. 267–268 (1996). For the first polymerization process, the presence of (II) reduces the amount of alkylaluminum compound that must be added to the process to achieve good polymer yields, and/or the Ni or Pd compound which is used is relatively stable and therefore may be stored for long periods and/or used under ambient conditions (e.g. no refrigeration needed). In addition to the advantages described for the first polymerization process, the second polymerization does not require the prior preparation of a complex of Ni or Pd with (I), but rather the Ni or Pd compounds used are readily available and relatively stable. Not having to prepare the Ni or Pd complex of (I) in a separate step is also economically advantageous.

In the Examples, the following abbreviations are used:

DSC—differential scanning calorimetry

Et—ethyl

Me—methyl

MMAO—modified methyl aluminoxane

OAc—acetate

Pr—propyl

Tg—glass transition temperature

Tm—melting point

EXAMPLES

Cyclopentene was purified by passage through a column of 5 Å molecular sieves, followed by passage through a column of alumina, and finally distillation under nitrogen from sodium metal.

Modified Methyl Aluminoxane [(MeAlO)ₙ] used in these experiments was purchased from Akzo as a 6.7 wt. % solution in toluene. The methyl aluminoxane has been modified by replacing about 25 mole percent of the methyl groups with isobutyl groups.

EXAMPLES 1–18 AND COMPARATIVE
EXAMPLES A–L

The following general procedure was used with compounds 1–6 below. In a nitrogen filled dry box, the catalyst was suspended in cyclopentene (molar ratio=10,000:1 unless otherwise noted). (II) and hydrocarbylation compound (HCC) were then added in rapid succession; molar ratios based on nickel or palladium are noted in Table 1. Unless otherwise noted, (II) was added to the reaction mixture before the HCC. The resulting mixture was stirred at ambient temperature under nitrogen; in some instances, due to the amount of precipitated polymer it was impossible to stir the reaction for more than a few days. After the number of days indicated in Table 1, the reaction was quenched and the polymer completely precipitated by addition of methanol. The polymer was then washed with methanol/HCl and then acetone on a fritted filter, and dried. The total turnover number for each reaction (moles cyclopentene polymerized per mole of Ni or Pd) is indicated in Table 1.

It can be seen from Table 1 that addition of (II) such as $B(C_6F_5)_3$ and $AlCl_3$ allows for the successful use of alkylating agents such as $AlMe_3$, $AlEt_3$, $Al(OEt)Et_2$, and $ZnEt_2$; in the absence of (II), no product is observed.

DSC data for several examples are compiled in Table 2. In general, the melting points are broad and the Tm values given represent the approximate end of the melting transition.

TABLE 1
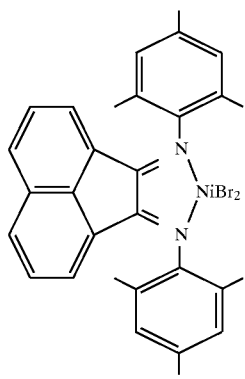
1
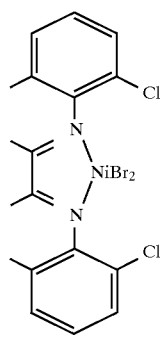
2
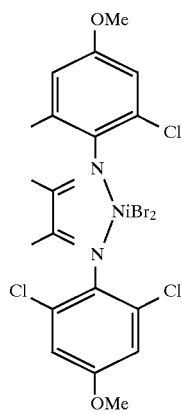
3
TABLE 1-continued
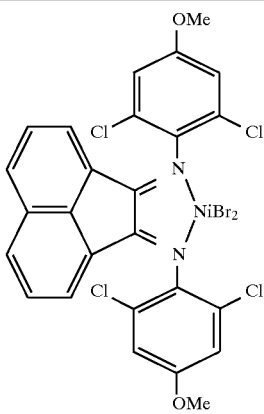
4
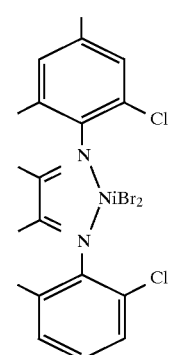
5
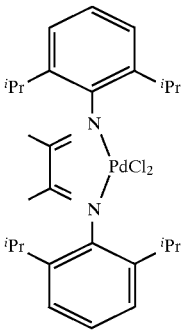
6
| Example | NI or Pd Compound | HCC (equiv) | (II) (equiv) | turnovers[a] (days) | Melt Index[b] |
|---|---|---|---|---|---|
| 1 | 1 | EtAlCl₂ (3) | B(C₆F₅)₃ (3) | 1833 (7) | 7.6 |
| 2[e] | 1 | EtAlCl₂ (3) | (Ph₃C)BF₄ (3) | 1827 (7) | 78 |
| A | 1 | EtAlCl₂ (50) | — | 1760 (7) | |
| B | 1 | EtAlCl₂ (3) | — | 846 (7) | 8.4 |
| 3 | 1 | AlEt₃ (3) | B(C₆F₅)₃ (3) | 3680 (7) | 14 |
| C | 1 | AlEt₃ (3) | — | 0 (5) | |
| 4 | 1 | AlEt₃ (3) | AlCl₃ (50) | 6031 (7) | high[c] |
| 5 | 1 | AlEt₃ (3) | AlCl₃ (3) | 1398 (7) | 6.2 |
| 6 | 1 | AlEt₃ (3) | Al(OTf)₃ (50) | 950 (7) | 54 |
| 7 | 1 | AlEt₃ (3) | AlBr₃ (50) | 7624 (7) | high[c] |
| 8 | 1 | AlMe₃ (3) | B(C₆F₅)₃ (3) | 4325 (7) | 14 |
| D | 1 | AlMe₃ (50) | — | 0 (7) | |
| 9[e] | 1 | Al(OEt)Et₂ (5) | B(C₆F₅)₃ (5) | 4232 (7) | 9.6 |

TABLE 1-continued

| | | | | | |
|---|---|---|---|---|---|
| E | 1 | Al(OEt)Et₂ (5) | — | 0 (6) | |
| 10 | 1 | ZnEt₂ (3) | B(C₆F₅)₃ (3) | 2880 (7) | 19 |
| F | 1 | ZnEt₂ (3) | — | 0 (8) | |
| 11 | 2 | AlEt₃ (3) | B(C₆F₅)₃ (3) | 5660 (7) | 2.1 |
| G[g] | 2 | (MeAlO)ₙ (100) | — | 1195 (5) | 7.6 |
| 12 | 2 | EtalCl₂ (3) | B(C₆F₅)₃ (3) | 3250 (7) | 1.7 |
| H[h] | 2 | EtAlCl₂ (50) | — | 5230 (8) | 3.6 |
| 13 | 2 | AlEt₃ (3) | AlCl₃ (50) | 4718 (7) | high[c] |
| 14[e] | 2 | Al(OEt)Et₂ (5) | B(C₆F₅)₃ (5) | 4688 (7) | 2.4 |
| 15 | 3 | AlEt₃ (3) | B(C₆F₅)₃ (3) | 2514 (7) | 1.0 |
| I | 3 | (MeAlO)ₙ (100) | — | 2020 (7) | |
| J | 3 | EtalCl₂ (50) | — | 5000 (2) | |
| 16 | 4 | AlEt₃ (3) | B(C₆F₅)₃ (3) | 3770 (7) | |
| K | 4 | EtalCl₂ (50) | — | 7210 (7) | |
| L | 4 | (MeAlO)ₙ (100) | — | 845 (7) | |
| 17 | 5 | ZnEt₂ (3) | B(C₆F₅)₃ (3) | 3462 (7) | 0.9[f] |
| 18 | 6 | AlEt₃ (3) | B(C₆F₅)₃ (3) | 1243 (7) | low[d] |

[a]"turnovers"=molar equivalents of monomer polymerized per molar equivalent of Ni or Pd [b]Melt indices were run with 8.5 kg weights at 300° C. MI value in Table 1 is defined as the mass of polymer (in grams) extruded in 10 minutes. The orifice was 2.095 mm in dia. and 8.000 mm long. MI value is inversely related to polymer molecular weight. [c]Melt index value too high to be recorded accurately; indicates relatively low molecular weight polymer. [d]Melt index value too low to be conveniently recorded; indicates relatively high molecular weight. [e]In this example, the alkylating agent was added to the reaction mixture before the Lewis acid. [f]MI recorded at 275° C. [g]Cyclopentene: Ni=5,000:1 [h]Cyclopentene: Ni=15,000:1

TABLE 2

| Example | ~Tm (end) °C. | ΔHf (J/g) |
|---|---|---|
| 1 | 285 | 17 |
| 2 | 260 | 6 |
| B | 285 | 8 |
| 3 | 277 | 12 |
| 6 | 280 | 15 |
| 9 | 280 | 22 |
| 10 | 280 | 24 |
| 11 | 265 | 16 |
| 12 | 255 | 12 |
| H | 260 | 17 |
| 14 | 263 | 15 |
| 15 | 290 | 18 |
| I | 291 | 18 |
| J | 291 | 31 |
| 16 | 325 | 32 |
| K | 335 | 9 |
| 17 | 275 | 22 |

EXAMPLE 19

This example demonstrates the use of Ni(acac)₂ (acac= MeCOCH=C(O)Me) as a precursor for cyclopentene polymerization. In a nitrogen filled glove box, Ni(acac)₂ (4 mg, 0.015 mmol) was dissolved in cyclopentene (10.0 g, 147 mmol) to give a pale, green-blue solution. To this was added 7 (6 mg, 0.015 mmol). To the resulting orange solution was added B(C₆F₅)₃ (23 mg, 0.045 mmol) to give a violet solution. Finally, 1.9M AlEt₃ in toluene (24 ul, 0.045 mmol) was added to the reaction mixture. The resulting magenta solution was stirred at ambient temperature for ~3 days with a magnetic stirbar; at the end of this time the reaction could no longer be stirred due to the amount of polycyclopentene that had precipitated. Seven days after the addition of AlEt₃, the reaction mixture was quenched and the polymer completely precipitated by addition of methanol under air. The precipitated polymer was washed with methanol/HCl and then acetone, and then dried to afford 4.00 g of polycyclopentene. DSC: Tm(end) ≈290° C. (19 J/g). This material was pressed at 300° C. to give a clear, tough film.

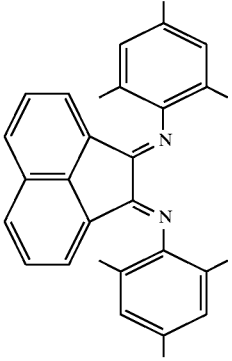

Comparative Example M

This experiment was identical to Example 19, except that B(C₆F₅)₃ was not present. Methanol was added to the reaction mixture after it had stirred at ambient temperature for 7 days; no polycyclopentene precipitated. This demonstrates that (II) [B(C₆F₅)₃ in 19] must be present for activity when AlEt₃ is used as the alkylating agent.

EXAMPLE 20

This example further demonstrates the use of Ni(acac)₂ as a catalyst precursor. In a nitrogen filled glove box, Ni(acac)₂ (4 mg, 0.015 mmol) and 8 (5 mg, 0.015 mmol) were dissolved in cyclopentene (10.0 g, 147 mmol) to give a pale-yellow solution. To this was added B(C₆F₅)₃ (23 mg, 0.045 mmol) followed by 1.9M AlEt₃ in toluene (24 ul, 0.045 mmol). The resulting orange solution was stirred at ambient temperature for 7 days with a magnetic stirbar. The reaction mixture was then quenched and the polymer completely precipitated by addition of methanol under air. The precipitated polymer was washed with methanol/HCl and then acetone, and then dried to afford 3.19 g of polycyclopentene. DSC: Tm(end) ≈270° C. (20 J/g).

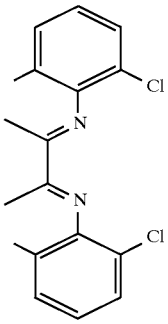

EXAMPLE 21

This example demonstrates the use of Ni[O₂C(CH₂)₆CH₃]₂ as a catalyst precursor. In a nitrogen filled glove box, Ni[O₂C(CH₂)₆CH₃]₂ (5 mg, 0.015 mmol) and 7 (6 mg, 0.015 mmol) were dissolved in cyclopentene (10.0 g, 147 mmol) to give an orange solution. To this was added B(C₆F₅)₃ (23 mg, 0.045 mmol) followed by 1.9M AlEt₃ in toluene (24 ul, 0.045 mmol). The resulting magenta solution was stirred at ambient temperature for 7 days with a magnetic stirbar. The reaction mixture was then quenched and the polymer completely precipitated by addition of methanol under air. The precipitated polymer was washed with methanol/HCl and then acetone, and then dried afford 1.6 g of polycyclopentene.

EXAMPLE 22

This example demonstrates the use of Pd(OAc)$_2$ (OAc is acetate) as a catalyst precursor. In a nitrogen filled glove box, Pd(OAc)$_2$ (3 mg, 0.013 mmol) and 9 (297 mg, 0.735 mmol) were dissolved in cyclopentene (10.0 g, 147 mmol). To this was added B(C$_6$F$_5$)$_3$ (23 mg, 0.045 mmol) followed by 1.9M AlEt$_3$ in toluene (24 ul, 0.045 mmol). The resulting cloudy, yellow solution was stirred with a magnetic stirbar at ambient temperature. Twenty-six hours after the addition of AlEt$_3$, the reaction mixture was quenched and the polymer completely precipitated by addition of methanol under air. The precipitated polymer was washed with methanol/HCl and then acetone, and then dried to afford 3.48 g of polycyclopentene. DSC: Tm(end)=250° C. (24 J/g); Tg=100.4° C. This material was pressed at 300° C. to give a tough film.

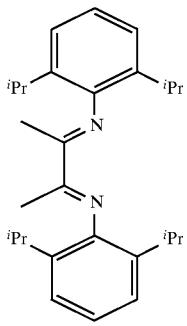

9

EXAMPLE 23

This example demonstrates the synthesis of ArN=C(CH$_3$)C(CH$_3$)=NAr (Ar=2,6-dichloro-4-methoxyphenyl). 2,6-dichloro-4-methoxylaniline (0.767 g, 4 mmol) and biacetyl (0.172 g, 2 mmol) were combined in 10 mL of anhydrous methanol containing 2 drops of concentrated sulfuric acid. After 48 hours, the precipitated product was isolated by filtration, washed with a 10:1 hexane/methanol mixture and dried in vacuo to give 0.476 g solid (55% yield). $^1$H NMR (CD$_2$Cl$_2$, 300 MHz): 2.1 (s, -CH$_3$, 6 H); 3.8 (s, -OCH$_3$, 6 H); 7.0 (s, aromatic H, 4H).

EXAMPLE 24

This example demonstrates the preparation of (ArN=C(CH$_3$)C(CH$_3$)=NAr)NiBr$_2$ (Ar=2,6-dichloro-4-methoxyphenyl), 3. ArN=C(CH$_3$)C(CH$_3$)=NAr (Ar=2,4,6-trimethylphenyl) (0.132 g, 0.304 mmol) was combined with NiBr$_2$(1,2-dimethoxyethane) (0.094 g, 0.304 mmol) in 4.6 mL of anhydrous methylene chloride under nitrogen in a dry box. After stirring for 168 hours, the solvent was decanted from the dark purple crystalline product. The product was washed 3×with pentane and dried in vacuo.

EXAMPLE 25

This example demonstrates the preparation of ArN=C(An)C(An)=NAr (Ar=2,6-dichloro-4-methoxyphenyl). 2,6-dichloro-4-methoxylaniline (2.18 g, 11.35 mmol) and acenapthenequinone (1.03 g, 5.63 mmol) were combined in 20 mL of anhydrous methanol containing 3 drops of concentrated sulfuric acid. After 48 hours, the precipitated product was isolated by filtration, washed with hexane followed by methanol, and dried in vacuo to give 2.47 g solid. $^1$H NMR showed this product to be a 3:1 mixture of the desired diimine and the monoimine. A portion of this solid (1.89 g) was combined with 0.42 g (2.19 mmol) additional 2,6-dichloro-4-methoxyaniline in a mixture of methanol (20 mL) and chloroform (5 mL) containing 2 drops of formic acid. The mixture was refluxed for 6 hours and then cooled to 25° C. overnight. The precipitated product was isolated by filtration, washed with hexane followed by methanol, and dried in vacuo to give 1.70 g solid. TLC showed this to be a mixture of two compounds. A portion of the solid (1.50 g) was purified by column chromatography on silica gel 60. The crude material was loaded on the column as a chloroform solution, and then eluted with toluene. The first band (0.96 g after solvent evaporation) was the desired diimine. $^1$H NMR (CD$_2$Cl$_2$, 300 MHz): 3.77, 3.80, 3.88 (singlets, -OMe, total area=6.1 H); 6.8–8.3 (aromatic H, total area=9.9 H). The three methoxy peaks are consistent with isomers due to slow rotation about the N=C bond on the NMR time scale.

EXAMPLE 26

This example demonstrates the preparation of (ArN=C(An)C(An)=NAr)NiBr$_2$ (Ar=2,6-dichloro-4-methoxyphenyl), 4. ArN=C(An)C(An)=NAr (Ar=2,6-dichloro-4-methoxyphenyl) (0.23 g) was combined with NiBr2(1,2-dimethoxyethane) (0.136 g) in 7.5 mL of anhydrous methylene chloride. The reaction was shaken for 24 hours. About ⅔ of the solvent was removed by evaporation. The precipitated product was isolated by filtration on a fritted glass filter, washed with pentane on the filter, and dried in vacuo.

EXAMPLE 27

This example demonstrates the synthesis of ArN=C(CH$_3$)C(CH$_3$)=NAr (Ar=2-chloro-6-methylphenyl), which was used to synthesize catalyst 2. 2-Chloro-6-methylaniline (5.66 g, 40.0 mmol) biacetyl (1.72 g, 20.0 mmol) were dissolved in methanol (10 mL). To this was added 2–3 drops of formic acid. The mixture was brought to reflux for 8–9 h. Solvent was then removed to afford an oil. The oil was purified by chromatography on a silica gel column. The first band, after solvent removal, crystallized to give a light yellow solid. The solid was washed with small amount of methanol and vacuum dried to afford 0.5 g of product (7.5%) $^1$H NMR (CDCl$_3$): 7.3 (d, 2H); 7.15.(d, 2H); 6.98(t, 2H); 2.10 (m, 12H).

2 was prepared from (dimethoxyethane)NiBr$_2$ and the above ligand, in a manner analogous to that described in examples 24 and 26.

EXAMPLE 28

This Example demonstrates the synthesis of ArN=C(CH$_3$)C(CH$_3$)=NAr (Ar=2-chloro-4,6-dimethylphenyl), which was used to synthesize 5. 2-Chloro-4,6-dimethylaniline (12.45 g, 80.0 mmol) and biacetyl (3.44 g, 40.0 mmol) were dissolved in methanol (10 mL). To this was added 2–3 drops of formic acid. The mixture was brought to reflux for overnight. Solvent was then removed to afford an oil. The oil was purified by chromatography on a silica gel column. The first band, after solvent removal, crystallized to give a yellow solid which was identified as the desired product (0.71 g, %). $^1$H NMR (CDCl$_3$): 7.10 (s, 2H); 6.95 (s, 2H); 2.30 (s, 6H); 2.10 (s, 6H); 2.07 (s, 6H).

5 was prepared from (dimethoxyethane)NiBr$_2$ and the above ligand, in a manner analogous to that described in Examples 24 and 26.

EXAMPLE 29

This example further demonstrates the use of Pd(OAc)$_2$ as a catalyst precursor. In a nitrogen filled glove box, Pd(OAc)$_2$ (3 mg, 0.013 mmol) and 10 (256 mg, 2 0.735 mmol) were dissolved in cyclopentene (10.0 g, 147.0 mmol). To this was added B(C$_6$F$_5$)$_3$ (23 mg, 0.045 mmol) followed by 1.9M AlEt$_3$ in toluene (24 μl, 0.045 mmol). The reaction mixture was stirred by a magnetic stirbar at ambient temperature for approximately 5 h, after which time it could no longer be stirred due to the amount of precipitated polymer. Seven days after the addition of AlEt$_3$, the reaction mixture was quenched and the polymer completely precipitated by addition of methanol under air. The precipitated polymer was washed with methanol/HCl and then acetone, and then dried to afford 1.99 g of polycyclopentene. Melt Index on this sample under the same conditions as described in Table 1 was 0.37.

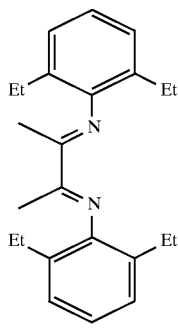

EXAMPLE 30

This example demonstrates the use of Pd(OAc)$_2$ as a catalyst precursor, in the presence of MMAO as the hydrocarbylation compound. In a nitrogen filled glove box, Pd(OAc)$_2$ (3 mg, 0.013 mmol) and 10 (256 mg, 0.735 mmol) were dissolved in cyclopentene (10.0 g, 147.0 mmol). To this was added 6.7 wt. % MMAO in toluene (0.700 mL, 1.47 mmol). The reaction mixture was stirred at ambient temperature for seven days. The reaction mixture was then quenched and the polymer completely precipitated by addition of methanol under air. The precipitated polymer was washed with methanol/HCl and then acetone, and then dried to afford 0.47 g of polycyclopentene. Melt Index on this sample under the same conditions as described in Table 1 was 16.

EXAMPLE 31

This example further demonstrates the use of Pd(OAc)$_2$ as a catalyst precursor. In a nitrogen filled glove box, Pd(OAc)$_2$ (3 mg, 0.013 mmol) and 11 (116 mg, 0.334 mmol) were dissolved in cyclopentene (10.0 g, 147.0 mmol). To this was added B(C$_6$F$_5$)$_3$ (23 mg, 0.045 mmol) followed by followed by 1.9 M AlEt$_3$ in toluene (24 μl, 0.045 mmol). The reaction mixture was stirred by a magnetic stirbar at ambient temperature; after several hours it could no longer be stirred due to the amount of precipitated polymer. Three days after the addition of AlEt$_3$, the reaction mixture was quenched and the polymer completely precipitated by addition of methanol under air. The precipitated polymer was washed with methanol/HCl and then acetone, and then dried to afford 3.36 g of polycyclopentene.

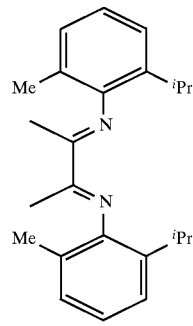

EXAMPLE 32

This example demonstrates the use of Pd(acac)$_2$ [acac= MeCOCH=C(O)Me] as a catalyst precursor. In a nitrogen filled glove box, Pd(acac)$_2$ (4–5 mg, [18] 0.015 mmol) and 11 (128 mg, 0.368 mmol) were dissolved in cyclopentene (10.0 g, 147.0 mmol). To this was added B(C$_6$F$_5$)$_3$ (23 mg, 0.045 mmol) followed by followed by 1.9M AlEt$_3$ in toluene (24 μl, 0.045 mmol). The reaction mixture was stirred by a magnetic stirbar at ambient temperature; after five hours it could no longer be stirred due to the amount of precipitated polymer. Three days after the addition of AlEt$_3$, the reaction mixture was quenched and the polymer completely precipitated by addition of iso-propanol and methanol under air. The precipitated polymer was washed with methanol/HCl and then acetone, and then dried to afford 4.84 g of polycyclopentene.

EXAMPLE 33

This example demonstrates polymerization of 1-hexene. In a nitrogen filled glovebox, 6 (28 mg, 0.048 mmol) was suspended in 1-hexene (2.00 g, 23.8 mmol). To this was added B(C$_6$F$_5$)$_3$ (73 mg, 0.14 mmol) followed by followed by 1.9M AlEt$_3$ in toluene (75 μl, 0.14 mmol). The reaction mixture became noticeably warm and viscous upon addition of AlEt$_3$. The reaction mixture was stirred overnight and then quenched by addition of iso-propanol under air. The polymer was completely precipitated by addition of methanol/HCl, and dried to afford 0.69 g of poly(1-hexene) as an extremely viscous oil. Olefin end-groups could not be detected in the room temperature $^1$H NMR spectrum of the polymer recorded in CDCl$_3$.

COMPARATIVE EXAMPLE N

This example was identical to Example 33, except that B(C$_6$F$_5$)$_3$ was not present. Methanol was added to the reaction mixture after it had stirred at ambient temperature overnight; no poly(1-hexene) precipitated. This demonstrates that in this reaction (II) must be present for activity when AlEt$_3$ is used as the alkylating agent.

What is claimed is:

1. A process for the polymerization of olefins, comprising, contacting, at a temperature of about −100° C. to about +200° C., a Ni (II) or Pd (II) complex of (I),

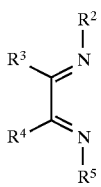

(I)

a metal containing hydrocarbylation compound, and a compound (II) selected from the group consisting of $B(C_6F_5)_3$, $AlCl_3$, $AlBr_3$, $Al(OTf)_3$, and $(R^{13}R^{14}R^{15}C)Y$, with an olefin, wherein:

said olefin is selected from the group consisting of ethylene, an olefin of the formula $R^{17}CH=CH_2$ or $R^{17}CH=CHR^{17}$, cyclobutene, cyclopentene, and a norbornene;

$R^2$ and $R^5$ are each independently aryl or substituted aryl, provided in both $R^2$ and $R^5$ at least one of the carbon atoms bound to a carbon atom bound directly to an imino nitrogen atom does not have any hydrogen atoms bound to it;

$R^3$ and $R^4$ are each independently hydrogen, hydrocarbyl, substituted hydrocarbyl, or $R^3$ and $R^4$ taken together are hydrocarbylene or substituted hydrocarbylene to form a carbocyclic ring;

$R^{13}$, $R^{14}$ and $R^{15}$ are each independently aryl or substituted aryl;

each $R^{17}$ is independently hydrocarbyl or substituted hydrocarbyl provided that any olefinic bond in said olefin is separated from any other olefinic bond or aromatic ring by a quaternary carbon atom or at east two saturated carbon atoms; and Y is a relatively noncoordinating anion.

2. A process for the polymerization of olefins, comprising, contacting a Ni (II) or Pd (II) salt with (I),

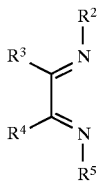

(I)

a metal containing hydrocarbylation compound, and optionally a compound (II) selected from the group consisting of $B(C_6F_5)_3$, $AlCl_3$, $AlBr_3$, $Al(OTf)_3$, and $(R^{13}R^{14}R^{15}C)Y$, with an olefin, wherein:

said Ni (II) or Pd (II) salt is selected from the group consisting of $Ni(O_2CR^7)_2$, $Ni[R^8COCH=C(O)R^8]_2$, $NiX_2$, $L^1L^2NiX_2$, $Ni(OR^{18})_2$, $Pd(O_2CR^9)_2$, $Pd[R^{10}COCH=C(O)R^{10}]_2$, $PdX_2$, $L^1L^2PdX_2$, and $Pd(OR^{19})_2$;

said olefin is selected from the group consisting of ethylene, an olefin of the formula $R^{17}CH=CH_2$ or $R^{17}CH=CHR^{17}$, cyclobutene, cyclopentene, and a norbornene;

$R^2$ and $R^5$ are each independently aryl or substituted aryl, provided in both $R^2$ and $R^5$ at least one of the carbon atoms bound to a carbon atom bound directly to an imino nitrogen atom does not have any hydrogen atoms bound to it;

$R^3$ and $R^4$ are each independently hydrogen, hydrocarbyl, substituted hydrocarbyl, or $R^3$ and $R^4$ taken together are hydrocarbylene or substituted hydrocarbylene to form a carbocyclic ring;

$R^{13}$, $R^{14}$ and $R^{15}$ are each independently aryl or substituted aryl;

each $R^{17}$ is independently hydrocarbyl or substituted hydrocarbyl provided that any olefinic bond in said olefin is separated from any other olefinic bond or aromatic ring by a quaternary carbon atom or at least two saturated carbon atoms;

each $R^{18}$ and $R^{19}$ is independently hydrocarbyl, substituted hydrocarbyl, or $R^{21}SO_3^-$;

each $R^7$, $R^8$, $R^9$ and $R^{10}$ is independently hydrocarbyl or substituted hydrocarbyl containing from 1 to 20 carbon atoms;

each X is independently halogen or $R^{21}SO_3^-$;

each $R^{21}$ is independently aryl, substituted aryl or perfluoroalkyl;

$L^1$ and $L^2$ are independently ligands capable of being displaced by (I), or taken together are a bidentate ligand that is capable of being displaced by (I); and Y is a relatively noncoordinating anion;

and provided that when said hydrocarbylation compound is other than an alkylaluminum compound containing one or more halogen atoms bound to an aluminum atom or $(R^{20}AlO)_q$ wherein $R^{20}$ is alkyl and q is a positive integer, (II) must be present.

3. The process as recited in claim 1 or 2 wherein said olefin is ethylene.

4. The process as recited in claim 1 or 2 wherein said olefin is norbornene.

5. The process as recited in claim 1 wherein said olefin is cyclopentene.

6. The process as recited in claim 1 or 2 wherein said olefin is a linear α-olefin.

7. The process as recited in claim 1 or 2 wherein a random or block copolymer is produced.

8. The process as recited in claim 1 or 2 wherein said hydrocarbylation compound is $MX_mR^6_n$, wherein:

M is Li, Mg, Zn[II], Al or Sn[IV];

each X is independently F, Cl, Br, I, or $OR^{12}$;

each $R^6$ is independently hydrocarbyl containing 1 to 20 carbon atoms;

m is 0 or a positive integer;

n is an integer of 1 or more;

m+n is the valence of M; and $R^{12}$ is hydrocarbyl containing 1 to 20 carbon atoms.

9. The process as recited in claim 1 or 2 wherein Y is BAF, $BF_4$, $B(C_6F_5)_4$, $SbF_6$ or $PF_6$.

10. The process as recited in claim 1 or 2 wherein $R^2$, $R^3$, $R^4$ and $R^5$ are:

| $R^2$ | $R^3$ | $R^4$ | $R^5$ |
|---|---|---|---|
| 2,6-i-PrPh | H | H | 2,6-i-PrPh |
| 2,6-i-PrPh | Me | Me | 2,6-i-PrPh |
| 2,6-i-PrPh | An | An | 2,6-i-PrPh |
| 2,6-MePh | H | H | 2,6-MePh |
| 2,6-EtPh | Me | Me | 2,6-EtPh |
| 2,4,6-MePh | Me | Me | 2,4,6-MePh |
| 2,6-MePh | Me | Me | 2,6-MePh |
| 2,6-MePh | An | An | 2,6-MePh |
| 2-t-BuPh | An | An | 2-t-BuPh |
| 2,5-t-BuPh | An | An | 2,5-t-BuPh |
| 2,4,6-MePh | An | An | 2,4,6-MePh |
| 2-Cl-6-MePh | Me | Me | 2-Cl-6-MePh |
| 2,6-Cl-4-OMePh | Me | Me | 2,6-Cl-4-OMePh |
| 2,6-Cl-4-OMePh | An | An | 2,6-Cl-4-OMePh |
| 2-i-Pr-6-MePh | An | An | 2-i-Pr-6-MePh |
| 2-i-Pr-6-MePh | Me | Me | 2-i-Pr-6-MePh |
| 2,6-t-BuPh | H | H | 2,6-t-BuPh |
| 2,6-t-BuPh | Me | Me | 2,6-t-BuPh |

-continued

| R² | R³ | R⁴ | R⁵ |
|---|---|---|---|
| 2,6-t-BuPh | An | An | 2,6-t-BuPh |
| 2-t-BuPh | Me | Me | 2-t-BuPh. |

11. The process as recited in claim 1 or 2 wherein said temperature is about 25° C. to about 100° C.

12. The process as recited in claim 1 or 2 wherein (II) is $(C_6F_5)_3B$.

13. The process as recited in claim 1 wherein said complex is

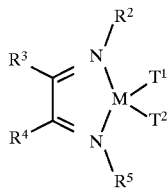

(VI)

wherein:
M is Ni or Pd;
$T^1$ and $T^2$ are each independently halogen, $R^7CO_2$, $R^8COCH=C(O)R^8$, or $OR^{18}$;
$R^2$ and $R^5$ are each independently aryl or substituted aryl, provided in both $R^2$ and $R^5$ at least one of the carbon atoms bound to a carbon atom bound directly to an imino nitrogen atom does not have any hydrogen atoms bound to it;
$R^3$ and $R^4$ are each independently hydrogen, hydrocarbyl, substituted hydrocarbyl, or $R^3$ and $R^4$ taken together are hydrocarbylene or substituted hydrocarbylene to form a carbocyclic ring;
each $R^{18}$ is independently hydrocarbyl; and
each $R^7$ and $R^8$ is independently hydrocarbyl or substituted hydrocarbyl containing from 1 to 20 carbon atoms.

14. The process as recited in claim 1 wherein a molar ratio of (II): Pd or Ni is about 0.5 to about 10, and a molar ratio of hydrocarbylation compound: Pd or Ni is about 0.5 to about 20.

15. The process as recited in claim 2 wherein:
when (II) is present a molar ratio of (II): Pd or Ni is about 0.5 to about 10, and a molar ratio of hydrocarbylation compound: Pd or Ni is 0.5 to about 20; and
when (II) is not present said molar ratio of hydrocarbylation compound: Pd or Ni is about 0.5 to about 200.

16. The process as recited in claim 13 wherein $T^1$ and $T^2$ are chlorine or bromine.

17. The process as recited in claim 1, 2 or 13 wherein:
said hydrocarbylation compound is $MX_mR^6_n$, wherein:
M is Li, Mg, Zn[II], Al or Sn[IV];
each X is independently F, Cl, Br, I, or $OR^{12}$;
each $R^6$ is independently hydrocarbyl containing 1 to 20 carbon atoms;
m is 0 or a positive integer;
n is an integer of 1 or more;
m+n is the valence of M; and
$R^{12}$ is hydrocarbyl containing 1 to 20 carbon atoms; and
said temperature is about 25° C. to about 100° C.; and
(II) is $(C_6F_5)_3B$.

18. The process as recited in claim 1, 2 or 13 wherein:
said hydrocarbylation compound is $MX_mR^6_n$;
M is Li, Mg, Zn[II], Al or Sn[IV];
each X is independently F, Cl, Br, I, or $OR^{12}$;
each $R^6$ is independently hydrocarbyl containing 1 to 20 carbon atoms;
m is 0 or a positive integer;
n is an integer of 1 or more;
m+n is the valence of M; and
$R^{12}$ is hydrocarbyl containing 1 to 20 carbon atoms;
said temperature is about 25° C. to about 100° C.; and
(II) is $(C_6F_5)_3B$; and
said olefin is one or more of ethylene, norbornene, cyclopentene, or a linear α-olefin.

19. The process as recited in claim 2 wherein each $R^{18}$ and $R^{19}$ is independently hydrocarbyl, each $R^7$, $R^8$, $R^9$ and $R^{10}$ is independently hydrocarbyl, and each X is independently chlorine or bromine.

* * * * *